United States Patent
Bishop et al.

(10) Patent No.: US 7,030,981 B2
(45) Date of Patent: Apr. 18, 2006

(54) METHOD AND APPARATUS FOR MEASURING BIREFRINGENT PARTICLES

(75) Inventors: James K. Bishop, Berkeley, CA (US); Christopher K. Guay, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 482 days.

(21) Appl. No.: 10/215,518

(22) Filed: Aug. 9, 2002

(65) Prior Publication Data

US 2004/0027664 A1 Feb. 12, 2004

Related U.S. Application Data

(63) Continuation of application No. PCT/US01/04440, filed on Feb. 8, 2001.

(60) Provisional application No. 60/181,959, filed on Feb. 10, 2000.

(51) Int. Cl.
*G01J 4/00* (2006.01)
(52) U.S. Cl. ...................... 356/368; 356/365
(58) Field of Classification Search ......... 356/364–365
See application file for complete search history.

(56) References Cited

U.S. PATENT DOCUMENTS

| | | | |
|---|---|---|---|
| 1,872,891 A | 8/1932 | Church et al. | |
| 3,283,644 A | 11/1966 | Saltzman | |
| 3,545,254 A | 12/1970 | Chassagne et al. | |
| 3,831,028 A * | 8/1974 | Keriman et al. | 356/365 |
| 3,856,408 A * | 12/1974 | Hill et al. | 356/365 |
| 4,379,634 A * | 4/1983 | Rosenthal | 356/365 |
| 4,572,676 A | 2/1986 | Biermans et al. | |
| 4,683,211 A | 7/1987 | Onizuka et al. | |
| 4,912,059 A * | 3/1990 | Newman et al. | 356/364 |
| 5,001,070 A | 3/1991 | Ivaska et al. | |
| 5,158,897 A | 10/1992 | Kurzinger | |
| 5,168,326 A * | 12/1992 | Tokieda et al. | 356/368 |
| RE35,355 E | 10/1996 | Ryan et al. | |
| 5,993,640 A | 11/1999 | Risse et al. | |
| 6,023,332 A | 2/2000 | Bergstrom et al. | |
| 6,072,629 A | 6/2000 | Fan et al. | |
| 6,628,388 B1 * | 9/2003 | Darrow et al. | 356/364 |

* cited by examiner

*Primary Examiner*—Layla G. Lauchman
(74) *Attorney, Agent, or Firm*—Joseph R. Milner

(57) ABSTRACT

A method and apparatus for measuring birefringent particles is provided comprising a source lamp, a grating, a first polarizer having a first transmission axis, a sample cell and a second polarizer having a second polarization axis. The second polarizer has a second polarization axis that is set to be perpendicular to the first polarization axis, and thereby blocks linearly polarized light with the orientation of the beam of light passing through the first polarizer. The beam of light passing through the second polarizer is measured using a detector.

14 Claims, 7 Drawing Sheets parallel polarizers crossed (90°) polarizers

METHOD AND APPARATUS FOR MEASURING BIREFRINGENT PARTICLES

CROSS-REFERENCE TO RELATED APPLICATIONS

This application is a continuation of a PCT application No. PCT/US01/04440, filed Feb. 8, 2001, which is in turn is based on a provisional application Ser. No. 60/181,959 filed Feb. 10, 2000, the contents of which are hereby incorporated by reference in their entirety.

STATEMENT REGARDING FEDERALLY SPONSORED RESEARCH OR DEVELOPMENT

The invention described and claimed herein was made in part utilizing funds supplied by the United States Department of Energy under contract No. DE-AC03-76SF000-98 between the U.S. Department of Energy and the Regents of the University of California. The government has certain rights to the invention.

BACKGROUND OF THE INVENTION

Field of the Invention

Particles and dissolved material produced by marine biota in the upper ocean subsequently sinks and becomes remineralized in deeper waters. This is commonly referred to as the "biological pump". The transport of biogenic carbon from the surface to deep ocean, as particles and dissolved forms of both oceanic and inorganic material is a fundamental component of the marine carbon cycle and plays a critical role in regulating the level of $CO_2$ in the Earth's atmospheres. Model simulations of the preindustrial global carbon cycle indicate that atmospheric $CO_2$ concentrations would be approximately 60% higher in the absence of marine biota. The potential for the oceanic uptake of anthropogenic $CO_2$ to change significantly as a result of climate-induced modifications to the biological pump, e.g. increased productivity due to warmer temperatures is an issue of key importance to the study of global climate change.

Our understanding of the biological pump is severely limited because conventional ship-based sampling methods, e.g. collecting particles by filtration using rosette-mounted bottles or large volume in situ filtration, cannot adequately capture the spatial and temporal variability of biomass and carbon species in the ocean. New technology and sampling techniques are necessary to advance the current state of knowledge regarding the functioning of the biological pump and its consequences for global carbon cycling. Accordingly the inventors have intensively investigated methods and apparatuses for the qualification and quantification of particulate matter. In particular, described herein are techniques for the investigation of particulate inorganic carbon. More particularly, described herein are techniques and equipment for the investigation of particulate inorganic carbon in seawater.

Particulate inorganic carbon (PIC) in seawater comprises biogenic particles of calcium carbonate ($CaCO_3$). PIC occurs as both calcite and aragonite polymorphs of $CaCO_3$ in the marine environment, ranging in concentration from less than 0.01 µmol $CaCO_3$ $L^{-1}$ in deep ocean waters to over 30 µmol $CaCO_3$ $L^1$ in open ocean surface waters during phytoplankton blooms.

The formation of PIC at seawater pH follows the general reaction:

$$2HCO_3^-(aq) + Ca^{2+}(aq) \Longleftrightarrow CaCO_3(s) + CO_2(aq) + H_2O(l) \quad (1)$$

From Equation 1, it is evident that PIC formation results in a net reduction of total dissolved inorganic carbon species ($CO_2$, $H_2CO_3$, $HCO_3^-$ and $CO_3^{2-}$, collectively referred to as $\Sigma CO_2$) and contributes to the flux of sinking particles that transport carbon from the surface to deep ocean (i.e., the biological pump). But PIC formation also decreases alkalinity and increases $CO_2$ in surface marine waters, thereby reducing the capacity of the ocean for taking up atmospheric $CO_2$. While it is clear that PIC plays an important role in marine carbon cycling, much remains unknown about the processes governing its formation, transport and remineralization. Central to the understanding of PIC in marine carbon cycling is the ability to accurately and precisely measure PIC as well as other carbon system compounds and particles. Accordingly the invention described herein provides for a method of measuring birefringent particles, particularly suspended PIC.

U.S. Pat. No. 5,993,640 describes a method of measuring the $CaCO_3$ content of a suspension by injecting an acid into the suspension and measuring the change in pH.

U.S. Pat. No. 5,001,070 discloses a method of determining the total carbonate content in a fluid by an electrochemical method.

U.S. Pat. No. 4,683,211 describes a method of measuring the concentration of $CaCO_3$ in a slurry by reacting the $CaCO_3$ with an acid, blowing a known flow rate of air into the slurry, and measuring the flow rate of the mixed gas and the amount of sampled slurry.

BRIEF SUMMARY OF THE INVENTION

Numerous investigations have been undertaken by the inventors to provide for a sufficient method of measuring particulate matter. Particularly, the inventors have investigated methods for determining PIC concentrations in seawater based on the optical property of birefringence. Birefringence refers to the ability of a mineral crystal to split an incident beam of linearly polarized light into two beams of unequal velocities (corresponding to two different refractive indices of the crystal) which subsequently recombine to form a beam of light that is no longer linearly polarized. The extreme birefringence of $CaCO_3$ makes it appear to light up when viewed through crossed polarizers. The extreme birefringence of calcium carbonate ($CaCO_3$) relative to other major components of marine particulate matter provides a basis for making optical in situ measurements of particulate inorganic carbon (PIC) in seawater. Because $CaCO_3$ particles dominate the mineral fraction of marine particulate matter and are much more birefringent than other major types of inorganic particles, it is expected that PIC will be the dominant source of any birefringence signal obtained from seawater.

Thus the invention described herein provides for a method of measuring birefringent particulate matter and an apparatus for accomplishing the method. Particularly, the invention provides for a method of measuring suspended particulate matter, and more particularly the invention provides for a method of measuring suspended PIC in seawater and an apparatus for accomplishing the method.

DETAILED DESCRIPTION OF THE PREFERRED EMBODIMENTS

Our understanding of PIC cycling has been severely limited by conventional ship-based sampling techniques—i.e., chemical analyses of particulate material filtered from seawater. This method of sampling cannot adequately assess the factors governing spatial and temporal variability of PIC in the oceans.

The invention described herein measures particulate matter, particularly suspended particulate matter and more particularly suspended particulate inorganic carbon in seawater. The method contemplated by the inventors involves placing polarizing means in front of a source lamp and also in front of a detector and orienting the two polarizing means such that their transmission axes are perpendicular to each other (i.e., transmission of incident light front a source lamp is minimized.) Various amounts of particles were suspended in water and placed in a sample cell between the two polarizers. A strongly linear relationship was observed between the amount of particles in suspension and the amount of transmitted light reaching the detector. Analyses of suspensions containing diatomaceous earth and mixtures of diatomaceous earth and $CaCO_3$ indicate that only minor interference results from the presence of non-birefringence particles.

By "optical sensor" it is meant a device that responds to a physical stimulus involving light and transmits a resulting impulse. Any optical sensor known in the art may be used with this method.

By "particulate" it is meant discrete fragments of matter, i.e. particles. Particle or particulate is meant to include a single particle or a plurality of particles or particulates.

By "inorganic carbon" it is meant carbon contained in compounds not classified as organic.

"Calcite" is meant to include the polymorph of the mineral calcium carbonate having rhombohedral structure.

"Aragonite" is meant to include the polymorph of the mineral calcium carbonate having orthorhombic structure.

By "extreme birefringence" it is meant that the birefringence of particulate inorganic carbon (i.e. calcite and argonite) is at least five times greater than the birefringence of other types of particulate material typically encountered in seawater.

By "polarizer", it is meant any optical device that transmits light with electric field vectors restricted to a single plane. It is contemplated that any polarizing technique known in the art will be suitable for the instant invention.

By "beam of light" is meant light of any wavelength.

By "cross polarized light" it is meant light that is transmitted through two polarizers whose transmission axes are oriented at right angles with respect to each other.

"Measuring" is meant to include qualitative and/or quantitative analysis.

"Medium" is meant to include any medium where particles are found in suspension, including homogeneous or homogeneous mediums.

Figure 1:
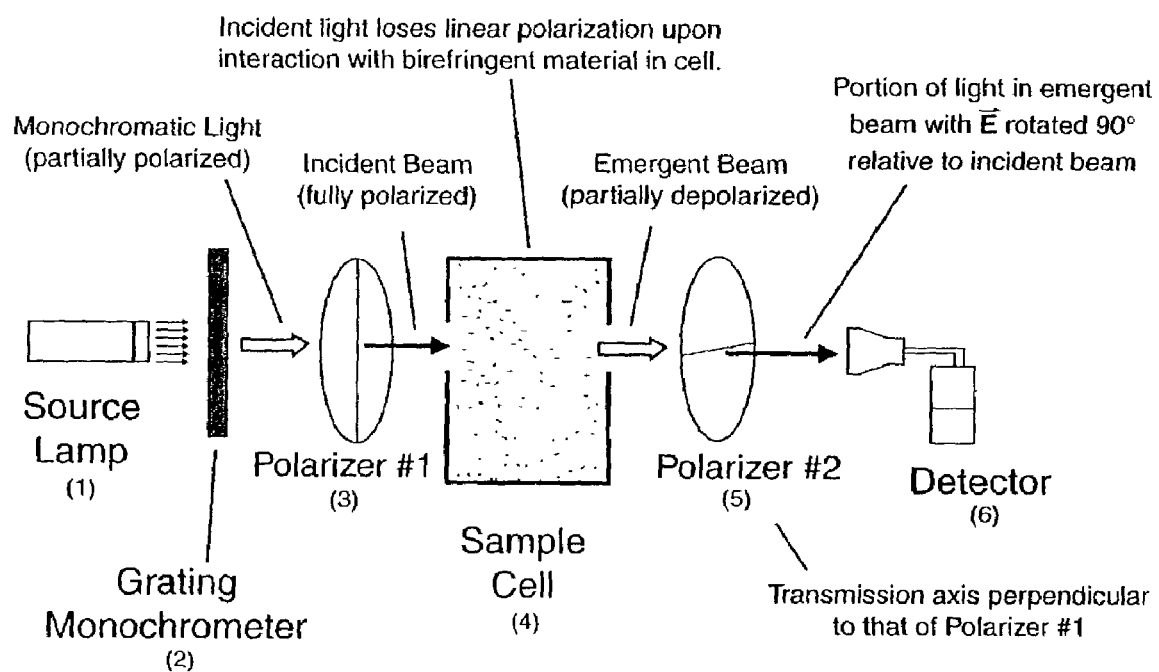
FIG. 1 is a schematic diagram of a spectrophotometer configured to measure samples in accordance with the invention.

The present invention will be more readily understood following a description of the method in conjunction with the Figures. In FIG. 1, a source lamp (1) is used to generate a source light. It is contemplated that any source lamp of light may be used. A grating (2) may be used to generate monochromatic, unpolarized light. It is to be understood that the invention does not require a narrow selection of wavelengths, rather it is desired that the wavelengths of the light source are in the range of effectiveness of the polarizer. A spectrophotometer can be used to select light at a wavelength where a particular kind of polarizer is effective. The monochromatic, unpolarized light is passed through a first polarizer (3) having a first transmission axis, resulting in a beam of light being linearly polarized. This beam of light is allowed to contact the sample. The sample may be birefringent particles or a suspension thereof. It is particularly preferred that the sample be a suspension of $CaCO_3$ in seawater. However, the method and apparatus described herein is designed and suitable for the analysis of any species exhibiting birefringence. This would include, but is not limited to a pipeline slurry and particles on a plain surface. By allowing the beam of light to contact the sample, it is contemplated that the light may indeed pass through the sample, which sample may be in a sample cell (4). However, it is contemplated that the light from the first polarizer only need to interact with the birefringent sample such that the birefringent sample splits the beam of light, removing the linear polarization. Light having interacted with the birefringent sample is then passed through a second polarizer (5), having a second polarization axis. The second polarizer has a second polarization axis that is set to be perpendicular to the first polarization axis, and thereby blocks linearly polarized light with the orientation of the beam of light passing through the first polarizer. What is actually measured is light passing through the first polarizer that has had its linear polarization removed by interaction with the birefringent particles in the sample. Light having interacted with the birefringent particles is no longer linearly polarized and therefore can pass through the second polarizer. The beam of light passing through the second polarizer is measured using a detector (6). Any detector capable or measuring light is suitable. The amount of light reaching the detector is proportional to the amount of birefringent sample in the cell.

Figure 2:
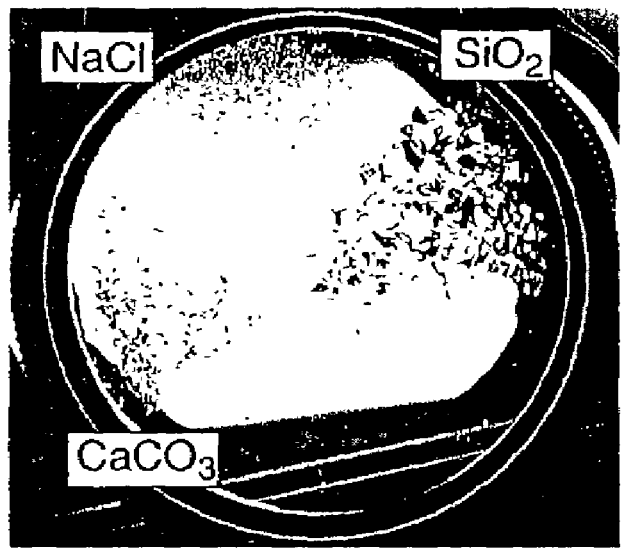
FIG. 2 shows the transmission of light through parallel and crossed polarizers by calcite ($CaCO_3$) and two non-birefringent minerals (NaCl and amorphous $SiO_2$).
Figure 2:
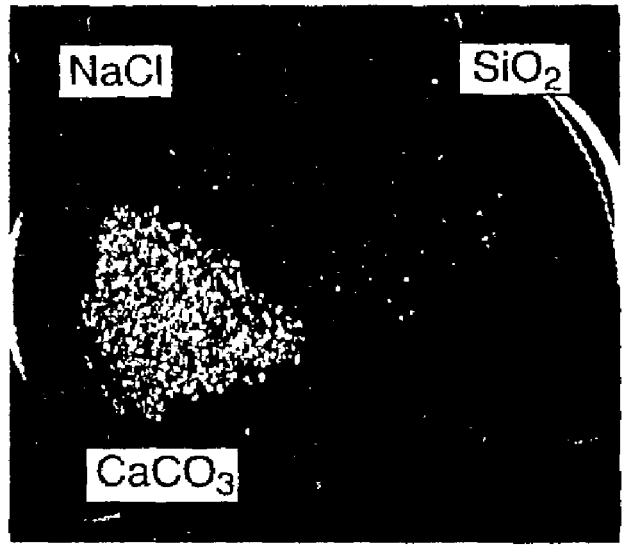

This concept is readily understood with reference to FIG. 2. If the polarizer axes are parallel to one another, all of the light passing through the sample cell will pass through the second polarizer; this includes light impinging on birefringent particles and non-birefringent particles. If the polarizer 1 and polarizer 2 axes are crossed (i.e., oriented at a 90 degree angle), only light that interacts with the birefringent particles will pass through the second polarizer.

Figure 3:
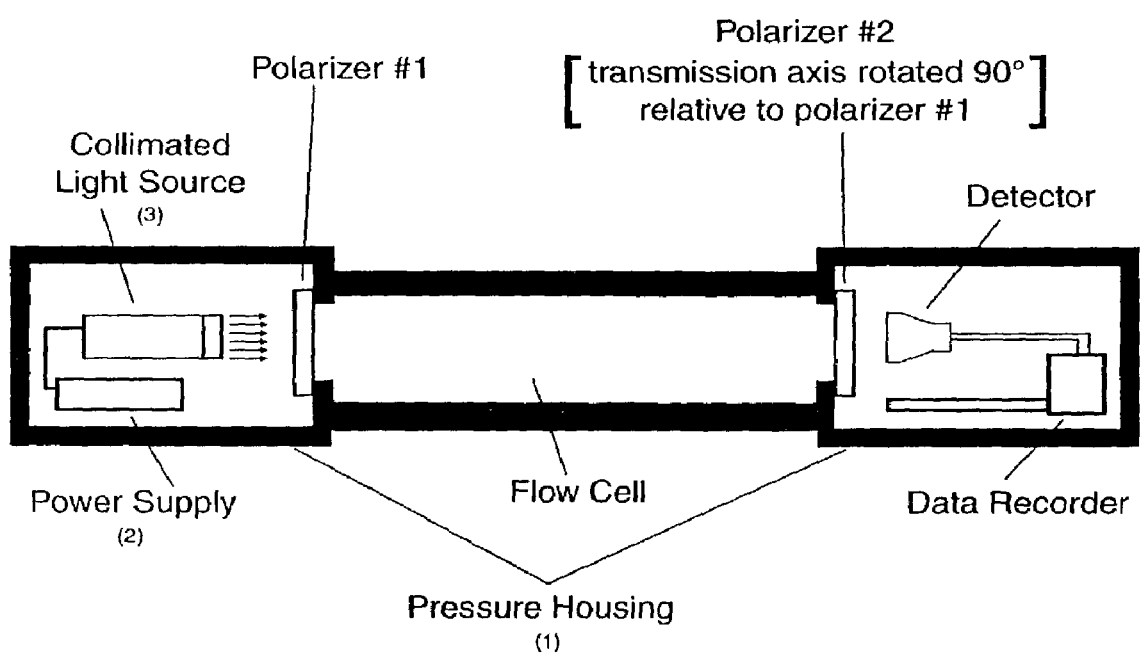
FIG. 3 is a schematic diagram of one possible design for an in situ optical PIC sensor.

The invention also contemplates a method and apparatus for performing both an in situ and not in situ analysis of birefringent particles, particularly PIC suspended in seawater. FIG. 3 displays a schematic of one possible design for an in situ PIC analyzer. The system is contained in a pressure housing (1). A power supply (2) provides power. A collimated light source (3) provides a beam of light. Polarizer 1 (4) is a first polarizer having a first transmission axis and Polarizer #2 (5) is a second polarizer having a second transmission axis. These polarizers function as described above. A detector (6) measures the output from the second polarizer and the data is recorded by a data recorder (7). It is contemplated that any apparatus that employs two polarizers having crossed transmission axes will be sufficient to accomplish the method of this invention. Any light source, detector and data recorder known in the art will work with this invention. The path length between polarizers is readily determinable by one having ordinary skill in the art using parameters routinely used in analytical instrumentation. Generally a path length of greater than zero cm up to 100 cm will be sufficient, but longer path lengths are contemplated, depending on the end use. The brightness of the collimated light source is readily determined by one having ordinary skill in the art depending on the desired application. It is also contemplated that the apparatus be can be deployed in a marine environment, autonomously, i.e. without human interaction.

The flow cell for the sample may comprise a flow-through sample chamber.

In the example described herein, a grating monochrometer is used. It is to be understood that any means for selecting a wavelength or range of wavelengths may be used, a non-limiting example of which is a selector or filter.

The apparatus can be designed such that the spatial dimensions and power requirements of the sensor are appropriate for long-term deployment on autonomous oceanographic platforms in addition to standard ship based deployment from a cable.

METHODS

The following method is described in conjunction with PIC suspended in seawater. However it is to be understood that the invention described herein can be used for any particles exhibiting birefringence, either in suspension or not.

Preparation of Sample Suspensions

Suspensions were prepared from two sources of solid material: calcareous marine sediment collected from a site in the Equatorial Pacific (0.95° N, 138.95° W, water depth=4287 m); and commercially available powdered diatomaceous earth (i.e., a source of non-birefringent amorphous $SiO_2$). The calcareous sediment was rich in coccoliths but also contained a significant amount of calcite from larger foraminifera shell fragments. In order to isolate the fraction of smaller particles that would most readily remain in suspension, the following settling procedure was applied. Roughly 0.06 g of each material was added to a separate polyethylene bottle containing 120 ml of saturated $CaCO_3$ solution (used to minimize dissolution of $CaCO_3$). The bottles were placed in an ultrasonic bath for 10 minutes to break up any large aggregates of solid material and then shaken vigorously to suspend the particles in solution. The bottles were allowed to sit undisturbed for 30 minutes, at which point the upper 100-ml portion of each solution was collected for further use and the remainder discarded. Approximately 29% and 41% of the original amounts of calcareous sediment and diatomaceous earth, respectively, were recovered by this procedure.

After fractionation, a 10-ml aliquot of each suspension was passed through a 0.4-µm polycarbonate membrane filter. The filters were dried and weighed to determine total suspended material (TSM) concentrations (Table 1). The filters were leached overnight in 2% $HNO_3$ and the leachate was analyzed for Ca by inductively coupled plasma atomic emission spectroscopy; PIC concentrations were determined for the suspensions as total acid-leachable Ca (Table 1). In the case of the diatomaceous earth suspension, it is likely that all of the Ca was not present as $CaCO_3$ and the reported PIC concentration should therefore be interpreted as an upper limit. The two pure suspensions were combined in different proportions and diluted with saturated $CaCO_3$ solution to give a series of mixed suspensions with varying ratios (by weight) of calcareous sediment to diatomaceous earth (Table 2).

TABLE 1

Composition of the pure calcareous sediment and diatomaceous earth suspensions.

| | TSM (mg ml$^{-1}$) | PIC (µmol $CaCO_3$ L$^{-1}$) | % $CaCO_3$ (by weight) |
|---|---|---|---|
| calcareous sediment | 0.192 | 1820 | 95% |
| diatomaceous earth | 0.250 | 1.97 | <1% |

TABLE 2

Composition of the mixed suspensions prepared from the pure calcareous sediment and diatomaceous earth suspensions.

| Calcareous Sediment/ Diatomaceous Earth Ratio (by weight) | TSM (mg ml$^{-1}$) | PIC (µmol $CaCO_3$ L$^{-1}$) | % $CaCO_3$ (by weight) |
|---|---|---|---|
| 1:0.5 | 0.096 | 613 | 64% |
| 1:1 | 0.126 | 602 | 48% |
| 1:2 | 0.188 | 604 | 32% |
| 1:10 | 0.243 | 228 | 9% |
| 1:50 | 0.248 | 65.5 | 3% |

Particle size distributions were determined for the pure calcareous sediment and diatomaceous earth suspensions using a Coulter Multisizer II equipped with a 30-µm aperture. Particle diameters ranged from 0.74 µm (the smallest size detectable) to 9.1 µm in the calcareous sediment suspension and to 9.8 µm in the diatomaceous earth suspension. The size distributions for both suspensions had similar shapes and were skewed towards the smaller-sized particles. Particles between 1 and 2 µm in diameter (i.e., typical coccolith size) comprised a greater proportion of the calcareous sediment suspension than the diatomaceous earth suspension. The difference between the total numbers of particles (and the total volumes they occupy) in the two suspensions is greater than expected based solely on the difference in their TSM values. This reflects the higher density of the calcareous material produced by coccolithophores and foraminifera relative to the more open-structured, siliceous material produced by diatoms.

Spectrophotometer Analyses

All analyses were performed on an Amersham Pharmacia Biotech Ultrospec 3000 Pro benchtop spectrophotometer equipped with a 1-cm path length optical silica sample cell. The spectrophotometer wavelength was set at 660 nm to match the red LED's commonly used in marine transmissometers (experiments conducted at different wavelengths yielded similar results). Transmittance (T) was measured and used to calculate absorbance (A) according to the standard relationship:

$$A = -\log_{10} T \quad (2)$$

To measure the birefringence of particles in suspension, the spectrophotometer was modified by installing a pair of Corning Polarcor linear polarizers. Because light from the source lamp was already partially polarized by the grating monochrometer, it was possible to maximize the intensity of the fully polarized beam incident upon the sample cell by rotating the polarizer between the source lamp and sample cell. The polarizer between the sample cell and the detector was rotated until the transmission of polarized light from the incident beam was minimized—i.e., the polarizers were crossed. Extinction ratios between $1.0 \times 10^4$ and $1.2 \times 10^4$ were typically achieved. To enable measurement of small signals above a near-zero background, the detector gain was set to approximately 275. The birefringence signal is reported as the ratio of the radiant power of the light reaching the detector (corrected for gain) to the radiant power of the light incident upon the front face of the sample cell.

Samples ranging in PIC between 12.1 and 1820 μmol $CaCO_3$ $L^{-1}$ were prepared by serial dilutions of each of the pure and mixed suspensions. Aliquots of the suspensions (ranging in volume from 0.02 to 3 ml) were added to the sample cell and diluted to approximately 3 ml total volume with saturated $CaCO_3$ solution. The contents of the cell were agitated with a pipette before each analysis. Data were acquired digitally for 60 seconds at a rate of approximately 1 Hz and an average value was calculated.

Samples were prepared and analyzed separately for the conventional (i.e., non-polarized) transmittance and birefringence measurements. Each analytical run consisted of 17–31 samples and lasted 1–2 hours. A reference cell containing particle-free, deionized water was run as a blank between every 5–10 samples. Data for the samples were blank-corrected by subtracting values linearly interpolated from the measured blanks. Samples prepared from the pure calcareous sediment suspension were analyzed during two separate runs performed approximately three weeks apart. Samples prepared from the pure diatomaceous earth suspension and the mixed suspensions were all analyzed during the same run.

RESULTS

Pure Calcareous Sediment and Diatomaceous Earth

Figure 4:
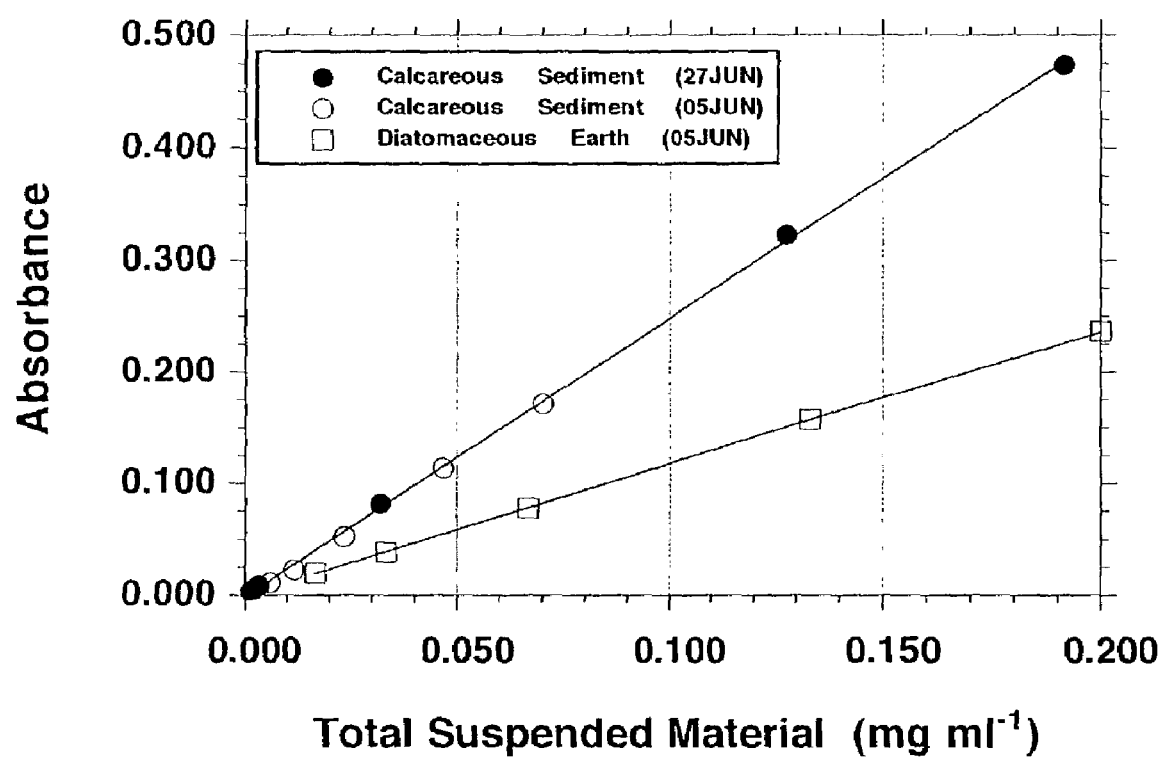
FIG. 4 is a graph showing the linear relationship between absorbance and total suspended material (TSM).

Absorbance readings for the blanks were less than 0.001. Linear relationships were observed between absorbance and TSM for the serial dilutions of the pure calcareous sediment and diatomaceous earth suspensions (FIG. 4). The slope for the calcareous sediment data (2.50 ml $mg^{-1}$) was more than twice as high as the slope for the diatomaceous earth data (1.18 ml $mg^{-1}$; Table 3).

TABLE 3

Summary of least-squares linear regressions for the serial dilutions of the pure calcareous sediment and diatomaceous earth suspensions.

| | Calcareous Sediment | Diatomaceous Earth |
|---|---|---|
| Absorbance | | |
| number of samples | 12 | 5 |
| slope (ml $mg^{-1}$) | 2.496 | 1.182 |
| standard error | 0.017 | 0.004 |
| intercept | −0.0017 | −0.0006 |
| standard error | 0.0013 | 0.0004 |
| correlation coefficient ($r^2$) | 0.999 | 1.000 |
| Birefringence Signal (initial linear response range—i.e., PIC < 450 μmol $CaCO_3$ $L^{-1}$) | | |
| number of samples | 9 | — |
| slope (L $μmol^{-1}$) | $5.37 \times 10^{-7}$ | — |
| standard error | $7.94 \times 10^{-9}$ | — |
| intercept | $-9.03 \times 10^{-7}$ | — |
| standard error | $1.58 \times 10^{-6}$ | — |
| correlation coefficient ($r^2$) | 0.998 | — |

The birefringence signal for the blanks ranged from $4.78 \times 10^{-5}$ to $5.06 \times 10^{-5}$ and drifted 1–3% over the course of an analytical run (Table 4).

TABLE 4

Birefringence signal for replicate samples and blanks.

| PIC (μmol $CaCO_3$ $L^{-1}$) | | Raw Birefringence Signal | Blank-Corrected Birefringence Signal | Standard Error For 60-second Acquisition |
|---|---|---|---|---|
| Blank | | $4.777 \times 10^{-5}$ | 0 | $4.3 \times 10^{-8}$ |
| | | $4.789 \times 10^{-5}$ | 0 | $5.1 \times 10^{-8}$ |
| | | $4.809 \times 10^{-5}$ | 0 | $4.6 \times 10^{-8}$ |
| | | $4.814 \times 10^{-5}$ | 0 | $5.4 \times 10^{-8}$ |
| | | $4.815 \times 10^{-5}$ | 0 | $5.7 \times 10^{-8}$ |
| | mean | $4.801 \times 10^{-5}$ | — | |
| | std dev | $1.683 \times 10^{-7}$ | — | |
| | Rel std dev | 0.35% | — | |
| Blank | | $5.062 \times 10^{-5}$ | 0 | $5.7 \times 10^{-8}$ |
| | | $5.009 \times 10^{-5}$ | 0 | $4.4 \times 10^{-8}$ |
| | | $4.975 \times 10^{-5}$ | 0 | $6.4 \times 10^{-8}$ |
| | | $4.901 \times 10^{-5}$ | 0 | $5.6 \times 10^{-8}$ |
| | mean | $4.987 \times 10^{-5}$ | — | |
| | std dev | $6.729 \times 10^{-7}$ | — | |
| | rel std dev | 1.35% | — | |
| 30.3 | | $6.65 \times 10^{-5}$ | $1.66 \times 10^{-5}$ | $2.2 \times 10^{-7}$ |
| | | $6.58 \times 10^{-5}$ | $1.62 \times 10^{-5}$ | $7.9 \times 10^{-8}$ |
| | | $6.53 \times 10^{-5}$ | $1.60 \times 10^{-5}$ | $1.5 \times 10^{-7}$ |
| | mean | $6.59 \times 10^{-5}$ | $1.63 \times 10^{-5}$ | |
| | std dev | $5.89 \times 10^{-7}$ | $2.80 \times 10^{-7}$ | |
| | rel std dev | 0.89% | 1.72% | |
| 303 | | $2.21 \times 10^{-4}$ | $1.71 \times 10^{-4}$ | $3.2 \times 10^{-7}$ |
| | | $2.22 \times 10^{-4}$ | $1.72 \times 10^{-4}$ | $2.3 \times 10^{-7}$ |
| | | $2.12 \times 10^{-4}$ | $1.62 \times 10^{-4}$ | $5.6 \times 10^{-7}$ |
| | mean | $2.18 \times 10^{-4}$ | $1.69 \times 10^{-4}$ | |
| | std dev | $5.68 \times 10^{-6}$ | $5.46 \times 10^{-6}$ | |
| | rel std dev | 2.60% | 3.24% | |
| 1210 | | $5.72 \times 10^{-4}$ | $5.22 \times 10^{-4}$ | $4.0 \times 10^{-7}$ |
| | | $5.75 \times 10^{-4}$ | $5.25 \times 10^{-4}$ | $3.0 \times 10^{-7}$ |
| | | $5.78 \times 10^{-4}$ | $5.29 \times 10^{-4}$ | $3.0 \times 10^{-7}$ |
| | mean | $5.75 \times 10^{-4}$ | $5.25 \times 10^{-4}$ | |
| | std dev | $3.08 \times 10^{-6}$ | $3.41 \times 10^{-6}$ | |
| | rel std dev | 0.54% | 0.65% | |

The blank-corrected birefringence signals for the samples were less than $1 \times 10^{-3}$—i.e., <0.1% of the radiant power of the incident light from the spectrophotometer source lamp.

Figure 6:
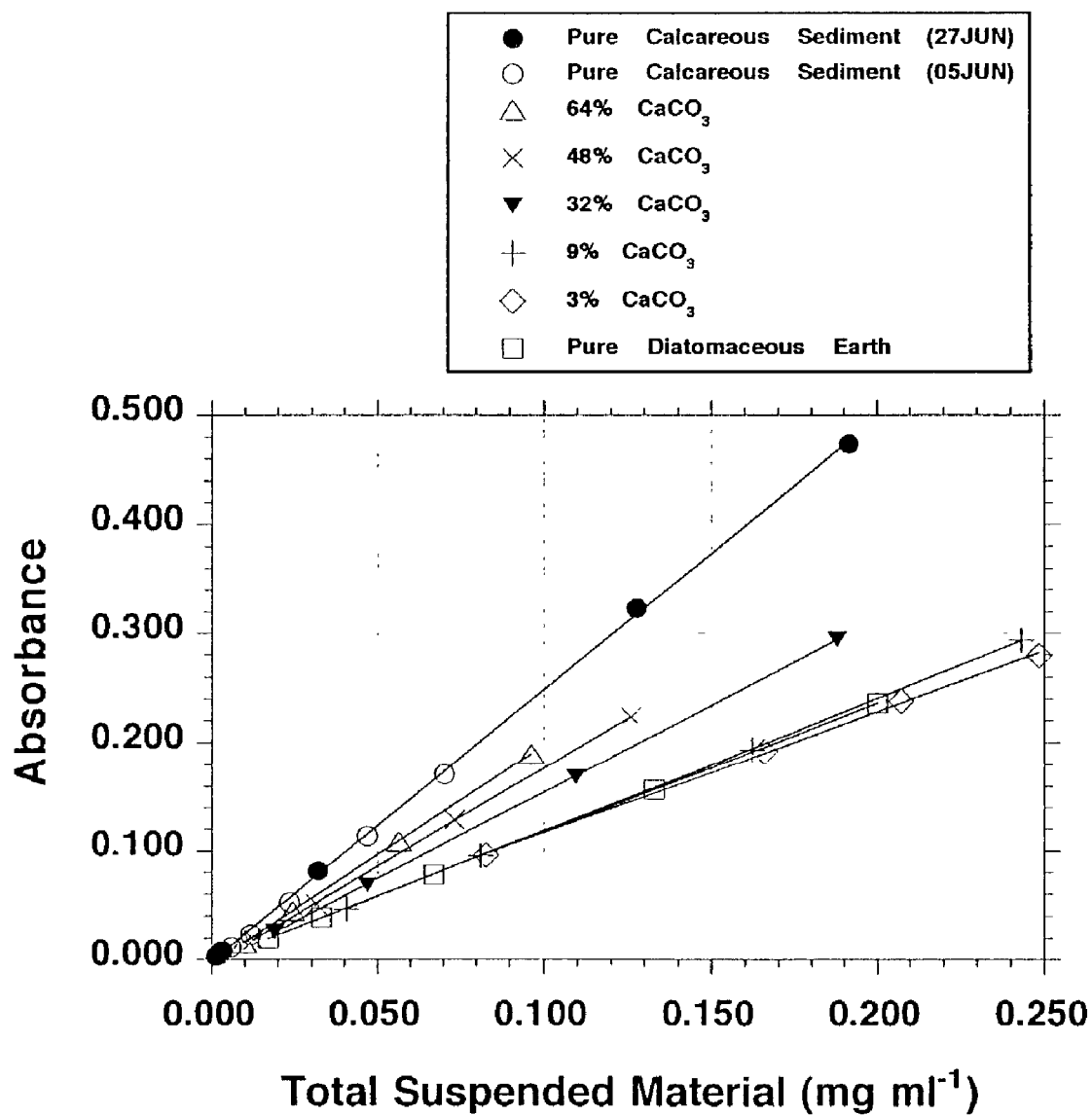
FIG. 6 shows absorbance at 660 nm for serial dilutions of the suspensions containing mixtures of calcareous sediment and diatomaceous earth. The solid lines indicate least-squares linear regressions of absorbance on TSM for the different suspensions. The observed slopes agree with values calculated from the $CaCO_3$ content of the mixtures and the slope values of the pure calcareous sediment and diatomaceous earth suspensions.

A positive relationship was observed between birefringence and PIC for the serial dilution of the pure calcareous sediment suspension (FIG. 6). The response initially followed a linear trend (slope=$5.37 \times 10^{-7}$ L$\mu$mol$^{-1}$; Table 3), falling off as PIC increased above 450 $\mu$mol CaCO$_3$ L$^{-1}$. The calcareous sediment data obtained on different days fell along the same trend, demonstrating the consistency of the measurements between different analytical runs. No detectable signal was observed for the samples prepared from the pure diatomaceous earth suspension.

Figure 5:
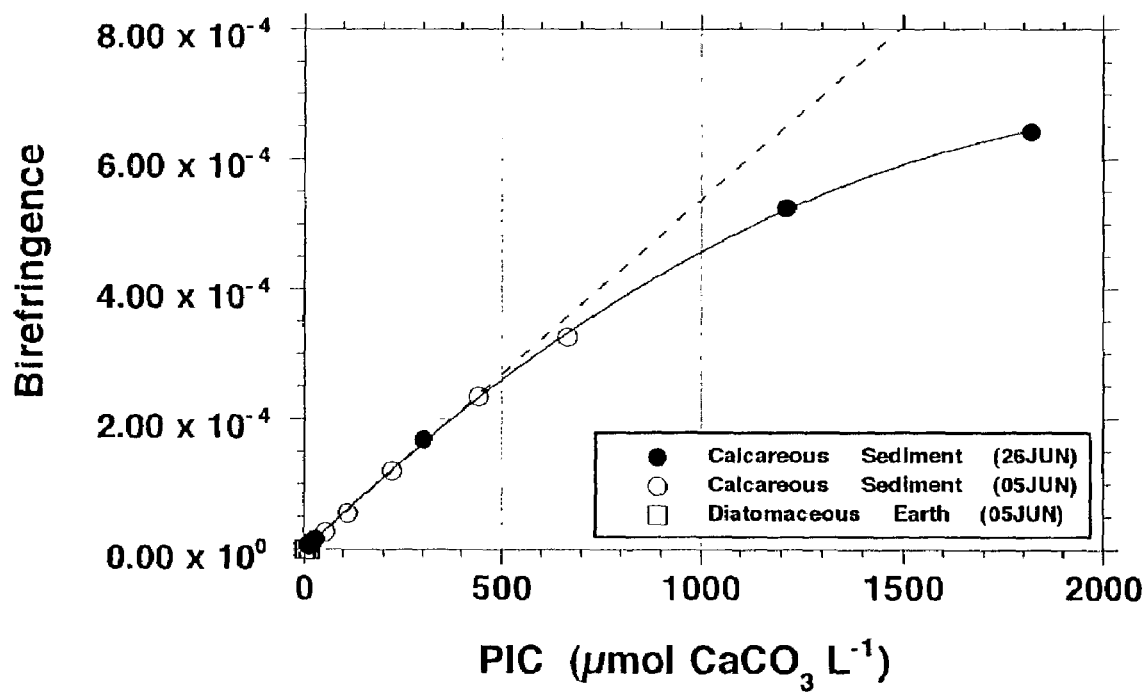
FIG. 5 is a graph of absorbance at 660 nm for serial dilutions of the pure calcareous sediment and diatomaceous earth suspensions. The solid lines indicate least-squares linear regressions of absorbance on TSM for the two suspensions.

The standard error of the birefringence signal over the 60-second data acquisition period was 2–8 times higher for the samples than for the blanks; the standard error was generally higher at the upper end of the analytical range and dropped considerably as PIC decreased below 100–200 $\mu$mol CaCO$_3$ L$^{-1}$ (Table 4). This indicates the greater variability inherent in a suspension of moving particles relative to particle-free solution. The minimum detectable birefringence signal (defined as three times the standard error of the blank signal over the 60-second acquisition period) ranged from $1.30 \times 10^{-7}$ to $1.93 \times 10^{-7}$. Based on the initial linear relationship between birefringence and PIC observed for the calcareous sediment (FIG. 5, Table 3), the minimum detectable birefringence signal is produced by values of PIC between 0.24 and 0.36 $\mu$mol CaCO$_3$ L$^{-1}$. This represents the lowest detection limit possible for a 60-second data acquisition period given the intrinsic signal noise of the modified spectrophotometer.

The precision of the method (2$\sigma$ for triplicate analyses of the 30.3, 303 and 1210 $\mu$mol CaCO$_3$ L$^{-1}$ samples) ranged from 1.3% to 6.5% of the blank corrected signal (Table 4). These values are a measure of uncertainty due to both signal noise and procedural error (i.e., instrument drift, pipetting inaccuracy, etc.). For the 30.3 $\mu$mol CaCO$_3$ L$^{-1}$ sample, the standard deviation of the triplicate analyses is of the same magnitude as the standard error of the average birefringence signal over the 60-second acquisition period for the individual analyses. The uncertainty in the measurement is therefore primarily due to signal noise at this concentration of PIC. For the 303 and 1210 $\mu$mol CaCO$_3$ L$^{-1}$ samples, the standard deviation of the triplicate analyses is roughly an order of magnitude higher than the standard error of the average birefringence signal over the 60-second acquisition period for the individual analyses. This indicates that most of the uncertainty in the measurement at higher concentrations of PIC is due to procedural error, with only a relatively small contribution from signal noise.

To verify that the birefringence signal was primarily due to the presence of CaCO$_3$ particles, undiluted pure calcareous sediment suspension was acidified and reanalyzed. Upon addition of HNO$_3$ to the sample cell, absorbance dropped from 0.474 to 0.013, in agreement with the 95% CaCO$_3$ content determined for the calcareous sediment material. Birefringence dropped from $6.42 \times 10^{-4}$ to $2.77 \times 10^{-6}$, indicating that virtually all (99.6%) of the signal was due to CaCO$_3$. The small residual signal is consistent with the expected presence of clay minerals and other weakly birefringent material in the calcareous sediment.

Mixtures of Calcareous Sediment and Diatomaceous Earth

Absorbance and TSM were linearly related for the serial dilutions of each of the suspensions containing mixtures of calcareous sediment and diatomaceous earth (FIG. 6). The slopes ranged from 1.12 to 2.00 ml mg$^{-1}$ (within the limits defined by the slopes for the pure calcareous sediment and diatomaceous earth suspensions) and increased in proportion to the CaCO$_3$ content of the suspensions.

Figure 7:
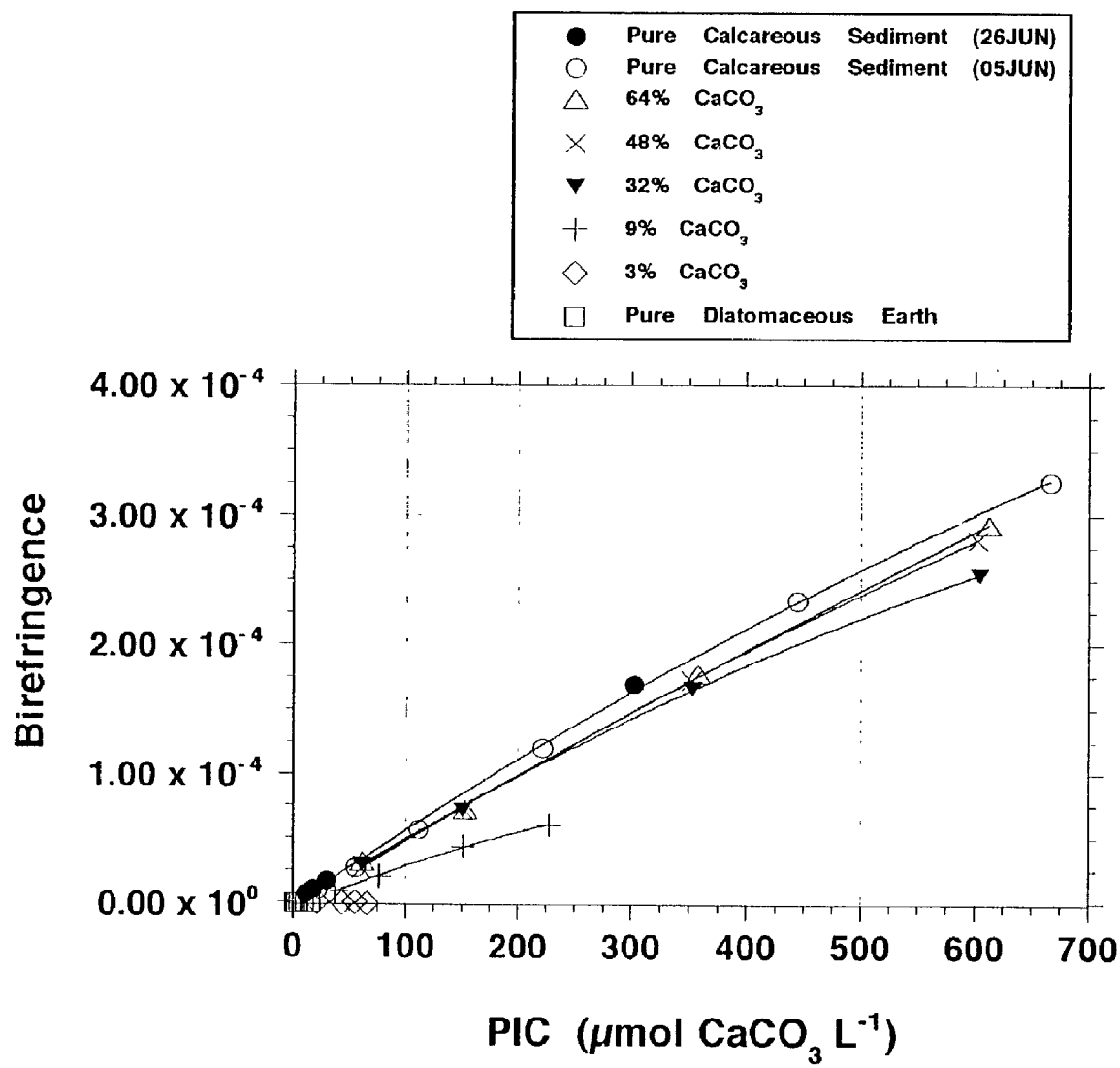
FIG. 7 shows birefringence for the serial dilutions of the suspensions containing mixtures of calcareous sediment and diatomaceous earth. Data obtained for the pure calcareous sediment and diatomaceous earth suspensions are also plotted for comparison. The two pure calcareous sediment samples with much higher PIC concentrations than the rest of the samples (1210 and 1820 µmol $CaCO_3$ $L^{-1}$) do not appear on this graph.

Birefringence and PIC were positively correlated for the serial dilutions of the mixed suspensions with CaCO$_3$ content$\geq$9% (FIG. 7). As was observed for the pure calcareous sediment suspension, the response fell off as PIC increased. Sensitivity decreased as the relative proportion of CaCO$_3$ in the suspensions decreased, dropping approximately 2-fold between the pure calcareous sediment suspension and the 9% CaCO$_3$ suspension. No detectable signal was observed for the samples prepared from the 3% CaCO$_3$ suspension, with the particular apparatus setup used for this example. It is contemplated that CaCO$_3$ samples well below 3% are readily detectable by an apparatus change or data handling technique readily available to one having ordinary skill in the art.

It is to be understood that in the foregoing example, the spectrophotometer was operated at a gain setting far above its normal operating range. In developing an in situ or ex situ apparatus for measuring birefringent samples, especially particles in suspension, the source lamp and detector apparatus and other instrument parameters, as well as data reduction techniques, are able to be optimized by one having ordinary skill in the art without undue experimentation with the specific intent of obtaining the most stable birefringence signal as possible.

The foregoing description is intended primarily for purposes of illustration. Although the invention has been described with respect to an exemplary embodiment thereof, it should be understood by those skilled in the art that the foregoing and various other changes, omissions, and additions in the form and detail thereof may be made therein without departing from the spirit and scope of the invention.

What is claimed is:

1. A method of analyzing a birefringent sample characterized by,
   generating a first beam of light using a first polarizer,
   said first polarizer having a first transmission axis,
   contacting a birefringent sample with the first beam of light, thereby creating a second beam of light,
   passing the second beam of light through a second polarizer,
   said second polarizer having a second transmission axis,
   measuring the light passing trough the second polarizer,
   where the first transmission axis is arranged to be perpendicular to the second transmission axis,
   wherein said sample is positioned in a flow-through sample chamber,
   and wherein said birefringent sample comprises a particle.

2. The method of claim 1, wherein the particle is suspended in a medium.

3. The method of claim 2, wherein the medium comprises a liquid.

4. The method of either of claim 2 or 3, wherein the medium comprises water or seawater.

5. The method of either of claim 2 or 3, wherein the particle comprises CaCO$_3$.

6. An apparatus for analyzing a birefringent sample characterized by having a first polarizer having a first transmission axis, and a second polarizer having a second transmission axis,
   said first polarizer and second polarizer arranged such that light emitted from the first polarizer impinges on a sample comprising a particle and is subsequently passed through the second polarizer, where said first transmission axis and said second transmission axis are perpendicular to each other, and wherein said sample is positioned in a flow-through sample chamber.

7. The apparatus of claim 6, wherein the particle is suspended in a medium.

8. The apparatus of claim 6, wherein the particle comprises a $CaCO_3$.

9. The apparatus of claim 7 or 8, wherein the medium comprises a liquid.

10. The apparatus either of claim 7 or 8, wherein the medium comprises water or seawater.

11. The apparatus of claim 7 or 8, wherein the particle comprises $CaCO_3$ suspended in water or seawater.

12. The apparatus of claim 7, wherein the particle comprises $CaCO_3$.

13. The apparatus of claim 9, wherein the medium comprises water or seawater.

14. The method of claim 4, wherein the particle comprises $CaCO_3$.

* * * * *